United States Patent [19]
Johnson

[11] Patent Number: 5,329,943
[45] Date of Patent: Jul. 19, 1994

[54] ENDOSCOPIC ASSISTED ABDOMINOPLASTY

[75] Inventor: Gerald W. Johnson, Houston, Tex.

[73] Assignees: Jeffrey W. Johnson, Monroe, La.; Lana L. Davis, Spring, Tex.

[21] Appl. No.: 89,774

[22] Filed: Jul. 12, 1993

[51] Int. Cl.$^5$ .............................................. B31B 1/00
[52] U.S. Cl. ................................... 128/898; 606/219; 606/142
[58] Field of Search ................... 128/897, 898; 604/49, 604/51, 902; 606/1, 119, 139, 142, 143, 144, 148, 219, 220

[56] References Cited

U.S. PATENT DOCUMENTS

| | | | |
|---|---|---|---|
| 4,941,623 | 7/1990 | Pruitt | 606/219 |
| 4,944,443 | 7/1990 | Oddsen et al. | 606/219 |
| 4,962,770 | 10/1990 | Agee et al. | 128/898 |
| 5,027,834 | 7/1991 | Pruitt | 128/898 |
| 5,181,907 | 1/1993 | Becker | 604/902 |
| 5,242,456 | 9/1993 | Nash et al. | 606/148 |

FOREIGN PATENT DOCUMENTS

| | | | |
|---|---|---|---|
| 1191061 | 11/1985 | U.S.S.R. | 128/898 |
| 1437005 | 11/1988 | U.S.S.R. | 128/898 |
| 1572543 | 6/1990 | U.S.S.R. | 128/898 |

Primary Examiner—Ralph Lewis
Attorney, Agent, or Firm—Neal J. Mosely

[57] ABSTRACT

A novel surgical procedure is an endoscopic assisted abdominoplasty. This procedure eschews the use of abdominal incisions and obtains the desired result with no visible scars on the abdomen of the patient. A traditional or standard abdominoplasty (also called a dermolipectomy of the abdomen) has always required a surgical incision in the abdomen followed by surgical removal of part of the skin, the underlying fat layer, and suturing the opening. The endoscopic assisted abdominoplasty shown herein uses two small incisions, one in the umbilicus for introduction of the surgical instruments, and a small incision within the pubic hair line for endoscopic observation and control of the procedure. While observing the procedure through the endoscope, the surgical instruments are inserted through the umbilicular incision to remove fat (by liposuction) and plicate and repair the muscles (by use of a tenaculum and fascial staples or a single instrument which combines the function of these instruments). After removal of the instruments, the small incisions are sutured and the skin layer allowed to retract and tighten. The procedure has had considerable success and leaves no visible scars, which is of great importance to most patients.

27 Claims, 10 Drawing Sheets

ENDOSCOPIC ASSISTED ABDOMINOPLASTY

BACKGROUND OF THE INVENTION

1. Field of the Invention

This invention related to new and useful surgical procedures and more particularly to an endoscopic assisted adbominoplasty which eschews the use of large abdominal incisions and leaves no visible scars on the patient.

2. Brief Description of the Prior Art

Abdominoplasty (sometimes called a dermolipectomy of the abdomen) is a procedure which has been known for more than one hundred years. The procedure has always required a surgical incision in the abdomen followed by surgical removal of part of the skin, plication of the fascia with suturing, and finally suturing of the incision in the skin.

"*Reconstructive Plastic Surgery*", Second Edition, Volume 7 "The Lower Extremity The Trunk The Genitourinary Tract, Chapter 92 "*Dermolipectomy of the Abdominal Wall, Thighs, Buttocks, and Upper Extremity*" by Ivo Pitanguy, M.D.; 1977 W.B. Saunders Company is a treatise on dermolipectomy of the abdomen. Several traditional or standard procedures are described and shown.

"ABDOMINOPLASTY" by Frederick M. Grazer, M.D. *Plastic and Reconstructive Surgery* 51 No. 6 June 1973 The Williams and Wilkins Company, Baltimore, Md. 21202, pp. 617-623, describes further procedures in abdominoplasty of the abdomen.

References are given in both publications to many additional reports on varied procedures for abdominoplasty or dermolipectomy of the abdomen.

Acknowledgement is made to both authors for the use of some of their material in describing traditional or standard procedures for abdominoplasty or dermolipectomy of the abdomen.

According to "*Reconstructive Plastic Surgery*", Second Edition, Volume 7, Chapter 92, p. 3800-3807, the first dermolipectomies of the abdominal wall were performed by surgeons who were repairing massive umbilical hernias. The dermolipectomy facilitated the herniorrhaphy and relieved the patient of a pendulous abdomen. A number of procedures are described which illustrate the development of this surgical procedure. The classic lipectomy incisions are shown in FIG. 92-2 on page 3802 of the text. These illustrations of the various incisions are reproduced herein as FIG. 1 of the drawings illustrating the prior art. The author of the text (Ivo Pitanguy, M.D.) reports an improved procedure using a lower abdomen incision to reduce the visibility of the resulting scar. In "ABDOMINOPLASTY" by Frederick M. Grazer, M.D. *Plastic and Reconstructive Surgery* 51 No. 6 June 1973, the author reports (at pp. 617-623) a modified Pitanguy technique which confines the final scar to the "bikini" area. For a more detailed description, one should consult the full text of the reference.

SUMMARY OF THE INVENTION

One of the objects of the invention is to provide a new and improved surgical procedure for abdominoplasty of the abdomen.

Another object of the invention is to provide a new and improved surgical procedure for abdominoplasty of the abdomen which is essentially free from visible scars.

Another object of the invention is to provide a new and improved surgical procedure for abdominoplasty of the abdomen which is easily performed and is essentially free from visible scars.

Another object of the invention is to provide a new and improved surgical procedure for abdominoplasty of the abdomen which relies on and allows the natural elasticity of the skin to cause the undermined skin to contract or shrink down to conform to the new abdominal wall, thereby not requiring the long incisions needed to remove skin and leaving long ugly scars.

Still another object of the invention is to provide a new and improved surgical procedure for abdominoplasty of the abdomen which combines several surgical techniques into a completely new procedure to avoid extensive scars on the abdomen.

Still another object of the invention is to provide a new and improved surgical procedure for abdominoplasty of the abdomen which utilizes small incisions hidden in the umbilicus and inside the pubic hair line.

Still another object of the invention is to provide a new and improved surgical procedure for abdominoplasty of the abdomen which utilizes a full and complete undermining of the abdominal skin and fat (as done in the most extensive traditional or standard abdominoplasty) made possible by use of the Endoscope.

Still another object of the invention is to provide a new and improved surgical procedure for abdominoplasty of the abdomen which includes a complete and effective plication or repair of the muscles and abdominal fascia, from the xyphoid process to the pubis, made possible by use of the Endoscope and fascial staples.

Yet another object of the invention is to provide a new and improved surgical procedure for abdominoplasty of the abdomen which does not use sutures to repair the abdominal muscles and fascia as the traditional or standard techniques require.

Yet another object of the invention is to provide a new and improved surgical procedure for abdominoplasty of the abdomen which includes a full and complete liposuction of the abdomen which is contraindicated in the traditional or standard abdominoplasty.

Yet another object of the invention is to provide a new and improved surgical procedure for abdominoplasty of the abdomen which is conducted by endoscopic procedure using surgical instruments inserted through an small incision in the umbilicus and endoscopic viewing through an instrument inserted through a small incision located below the pubic hair line.

Yet another object of the invention is to provide a new and improved surgical procedure for abdominoplasty of the abdomen which is conducted by endoscopic procedure using surgical instruments, e.g. liposuction, tenaculum, and fascial stapler, inserted through an small incision in the umbilicus and endoscopic viewing through an instrument inserted through a small incision located below the pubic hair line.

Other objects of the invention will become apparent from time to time throughout the specification and claims as hereinafter related.

These and other objects of the invention are accomplished by a novel surgical procedure which is an endoscopic assisted abdominoplasty which eschews the use of abdominal incisions and obtains the desired result with no visible scars on the abdomen of the patient. The endoscopic assisted abdominoplasty uses two small incisions, one in the umbilicus for introduction of the surgical instruments, and a small incision within the pubic hair line for endoscopic observation and control of the procedure. While observing the procedure through the endoscope, the surgical instruments are inserted through the umbilicular incision to remove fat (by liposuction) and plicate and repair the muscles (by use of a tenaculum and fascial staples). After removal of the instruments, the small incisions are sutured and the skin layer allowed to retract and tighten. The leaves no visible scars, which is of great importance to most patients.

DESCRIPTION OF THE PREFERRED EMBODIMENTS THE SURGICAL INSTRUMENTS

Referring to the drawings by numerals of reference, and more particularly to FIGS. 2-7, there are shown several instruments used in the procedure for endoscopic assisted abdominoplasty as described hereinafter. These instruments are all available commercially and have been used in other procedures. A combined tenaculum and stapling gun is contemplated for use in this procedure and is probably novel when developed.

A cervical tenaculum 10 (FIG. 2) comprises a pair of scissors type handles 12 with clamping ends 12 having teeth 13 which will bite into the fascia for plication and stapling in accordance with this procedure.

Figure 1A:
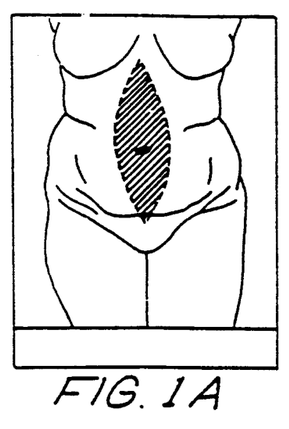
FIG. 1A is a plan view illustrating a prior art incision as used by Dr. Babcock in performing an abdominoplasty of the abdomen (taken from "Reconstructive Plastic Surgery", Second Edition, Volume 7, Chapter 92, p. 3802.
Figure 1B:
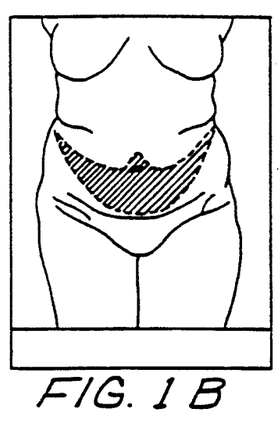
FIG. 1B is a plan view illustrating a prior art incision as used by Drs. Flesch-Thebesius Wheisheimer in performing an abdominoplasty of the abdomen (taken from "Reconstructive Plastic Surgery", Second Edition, Volume 7, Chapter 92, p. 3802.
Figure 1C:
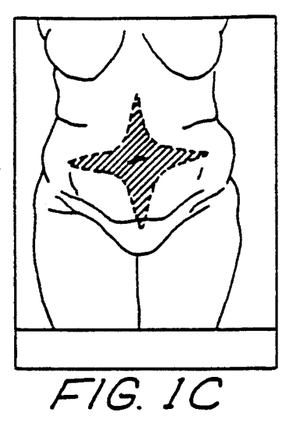
FIG. 1C is a plan view illustrating a prior art incision as used by Dr. Galtier in performing an abdominoplasty of the abdomen (taken from "Reconstructive Plastic Surgery", Second Edition, Volume 7, Chapter 92, p. 3802.
Figure 1D:
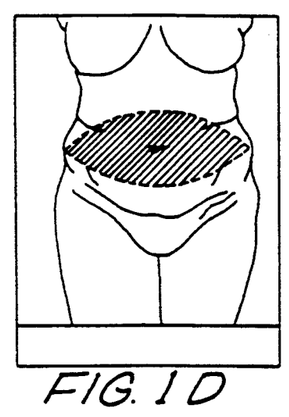
FIG. 1D is a plan view illustrating a prior art incision as used by Dr. Kelly in performing an abdominoplasty of the abdomen (taken from "Reconstructive Plastic Surgery", Second Edition, Volume 7, Chapter 92, p. 3802.
Figure 1E:
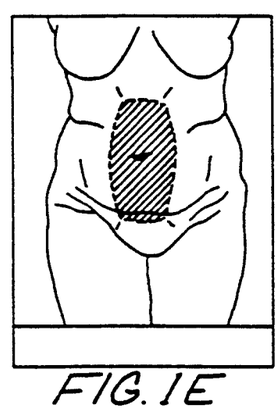
FIG. 1E is a plan view illustrating a prior art incision as used by Dr. Kuster in performing an abdominoplasty of the abdomen (taken from "Reconstructive Plastic Surgery", Second Edition, Volume 7, Chapter 92, p. 3802.
Figure 1F:
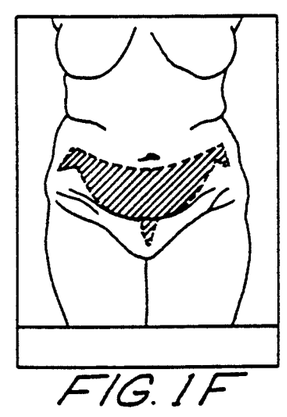
FIG. 1F is a plan view illustrating a prior art incision as used by Drs. Pick, Barsky and Gonzales-Ulloa in performing an abdominoplasty of the abdomen (taken from "Reconstructive Plastic Surgery", Second Edition, Volume 7, Chapter 92, p. 3802.
Figure 1G:
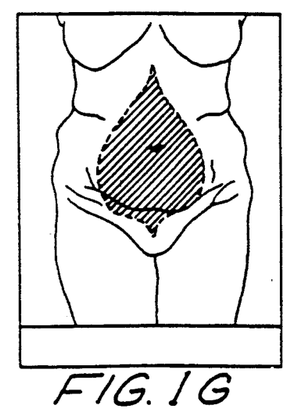
FIG. 1G is a plan view illustrating a prior art incision as used by Dr. Schepelmann in performing an abdominoplasty of the abdomen (taken from "Reconstructive Plastic Surgery", Second Edition, Volume 7, Chapter 92, p. 3802.
Figure 1H:
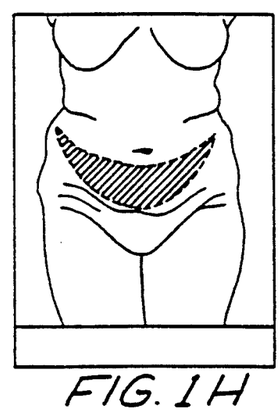
FIG. 1H is a plan view illustrating a prior art incision as used by Dr. Thorek in performing an abdominoplasty of the abdomen (taken from "Reconstructive Plastic Surgery", Second Edition, Volume 7, Chapter 92, p. 3802.
Figure 1I:
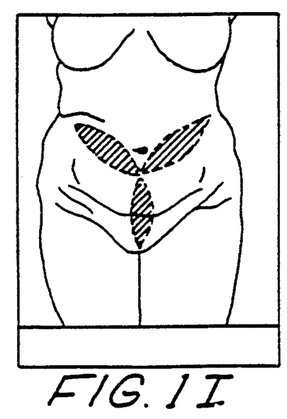
FIG. 1I is a plan view illustrating a prior art incision as used by Dr. Weinhold in performing an abdominoplasty of the abdomen (taken from "Reconstructive Plastic Surgery", Second Edition, Volume 7, Chapter 92, p. 3802.
Figures 2, 3, 4:
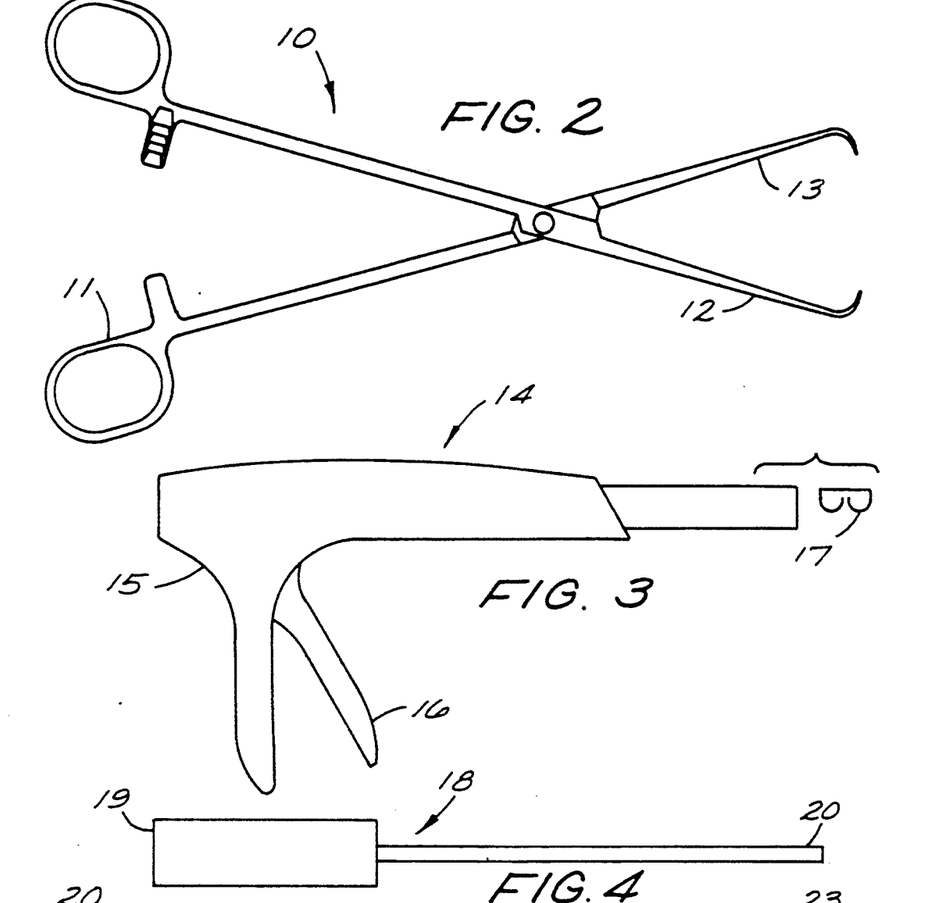
FIG. 2 is a plan view of a cervical tenaculum used in clamping the abdominal fascia during plication according to this invention.
FIG. 3 is a view in side elevation of a stapling gun and staple for fascial stapling in surgery.
FIG. 4 is a side elevation of an electrosurgical instrument having provision for electrosurgery or electrocauterization used in the surgical procedure of this invention.

A stapling gun 14 is shown in FIG. 3. Stapling gun 14 has a handle 15 and trigger or lever 16 for operation. Staple gun 14 uses stainless steel fascial staples 17 which are bent into a "B" or "8" shape in stapling to draw together the fascial layer being stapled. A suitable stapling gun is the Auto Suture ® disposable stapler manufactured by Auto Suture Co. and presently in use by general surgeons for fascial repair in open surgery. This inventor has an instrument in preparation for manufacture which combines the fascial stapler with the tenaculum so that the fascia may be plicated and stapled in a single step.

An electrosurgical instrument 18 is shown in FIG. 4. Instrument 18 has a handle 19 and cutting and/or cauterizing tip 20 for cutting and cauterizing in this surgical procedure.

Figures 5, 6:
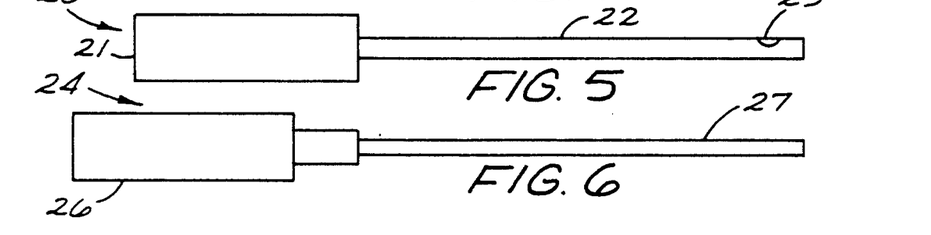
FIG. 5 is a side elevation of a tubular instrument for liposuction used in the procedure of this invention.
FIG. 6 is a side elevation of an instrument for endoscopic viewing and control of the surgical procedure of this invention.
Figure 7:
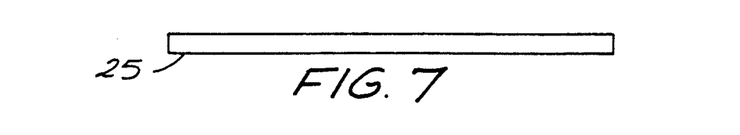
FIG. 7 is a side view of an endoscopic tube for introduction into the body and receiving the endoscopic viewing instrument shown in FIG. 6.

An liposuction instrument 21 is shown in FIG. 5. Instrument 28 has a handle 22 and tubular extension 22 with a side opening 23 for applying suction to remove the fatty layer underlying the skin prior to plication and stapling thereof.

A viewing instrument 24 and endoscopic tube 25 (FIGS. 6 and 7), preferably formed of surgical stainless steel or a hard plastic such as polyurethane or polycarbonate, comprises a handle 26 and endoscopic viewing tube 27 of sufficient length to extend through and out of the end of endotube 25 during use.

SURGICAL PROCEDURE FOR ENDOSCOPIC ASSISTED ABDOMINOPLASTY

FIG. 1 (collectively) may be referred to as illustrating traditional or standard procedures for abdominoplasty of the abdomen. FIGS. 1A–1I show nine different procedures for abdominoplasty of the abdomen involving incisions through the abdomen. These procedures have been developed in an effort to minimize scarring but have not been able to eliminate visible scars.

In FIGS. 8–19, a surgical procedure is described, utilizing the instruments of FIGS. 2–7 which is a totally new and innovative combination of techniques for abdominoplasty of the abdomen. All procedures (shown in FIGS. 8–19) were performed under general anesthesia.

Figure 8:
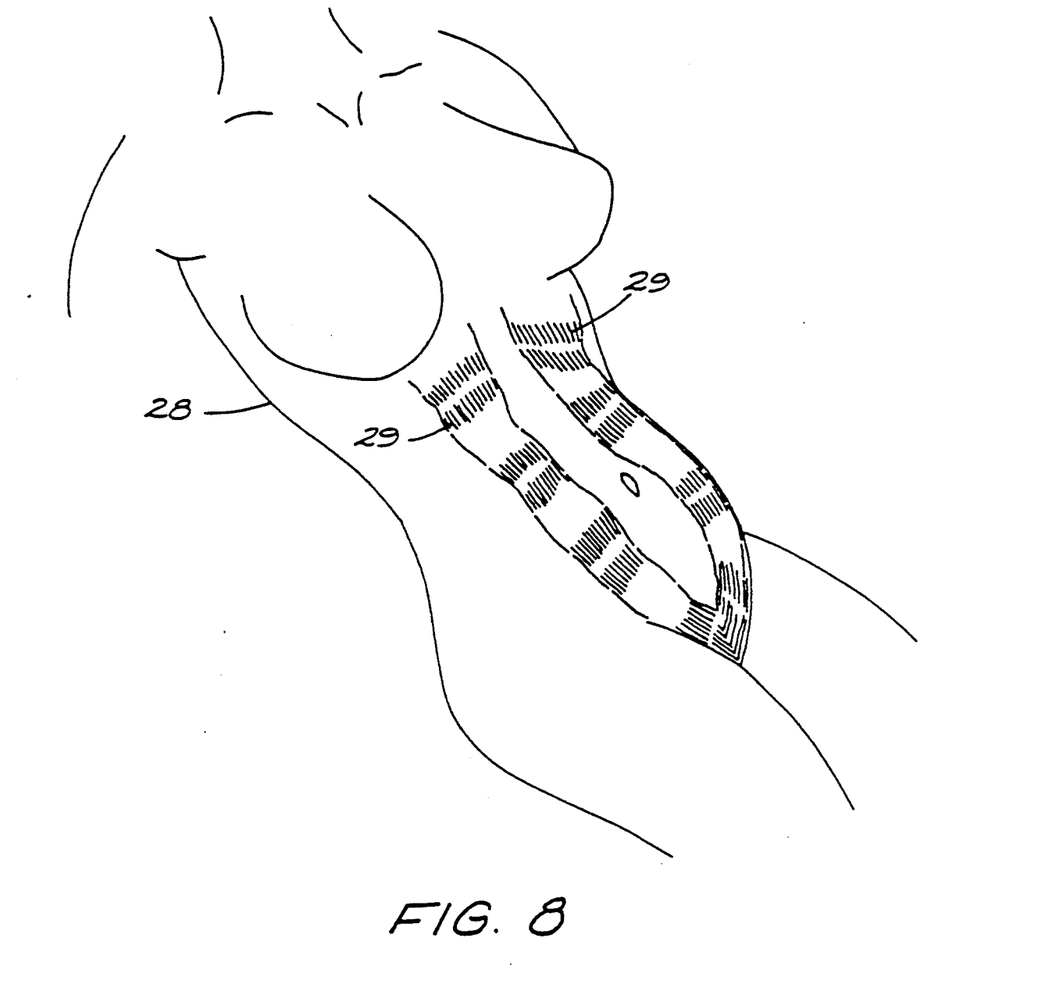
FIG. 8 is a schematic view of a female torso showing a condition with separation of the abdominal rectus muscles requiring the surgical procedure of this invention.

In FIG. 8, there is shown the torso 28 of a female patient needing an abdominoplasty of the abdomen. This view shows the fascial and muscular area beneath the skin an shows the separation of the abdominal rectus muscles 29 which results in the condition requiring surgical repair.

Figure 9:
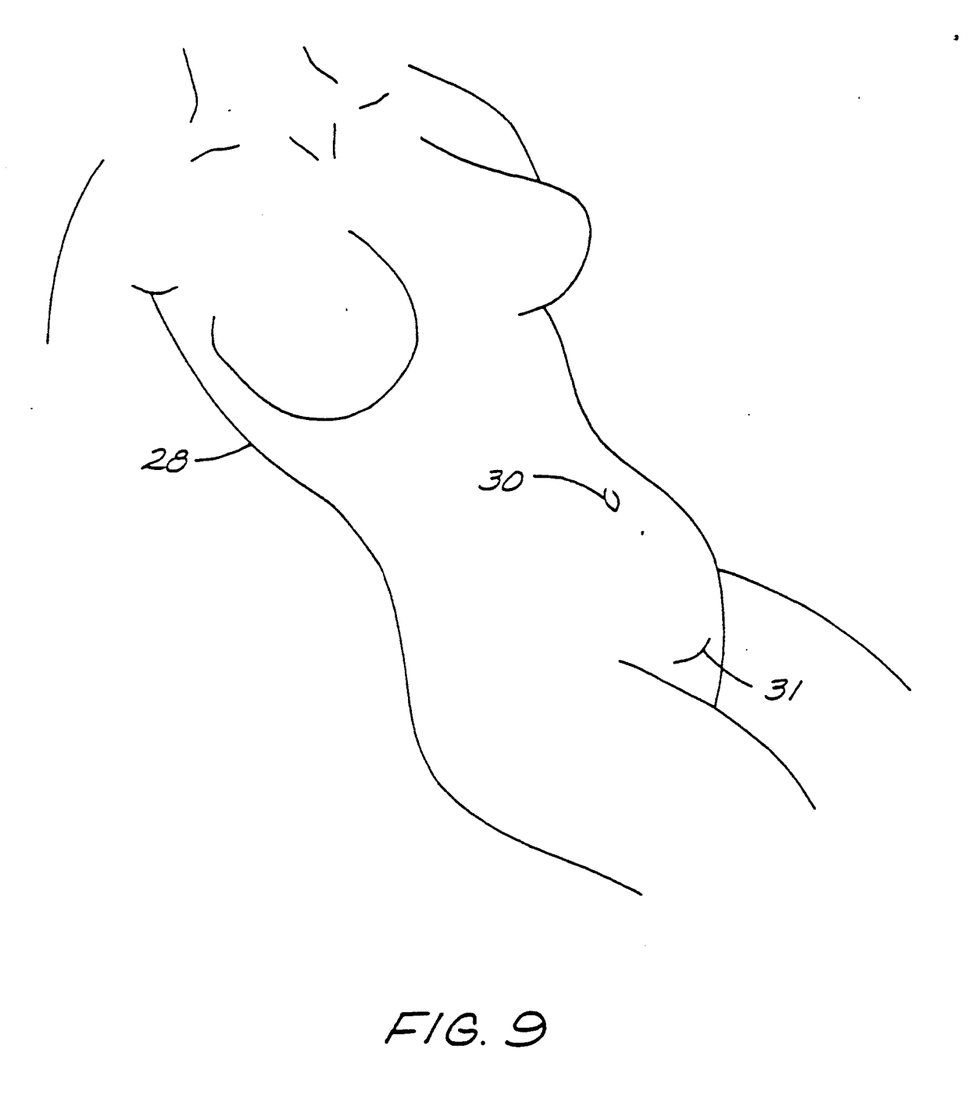
FIG. 9 is a schematic view of a female torso, as in FIG. 8, showing a short vertical umbilical incision and a short incision at the pubic hair line comprising initial steps in the surgical procedure of this invention.
Figure 10:
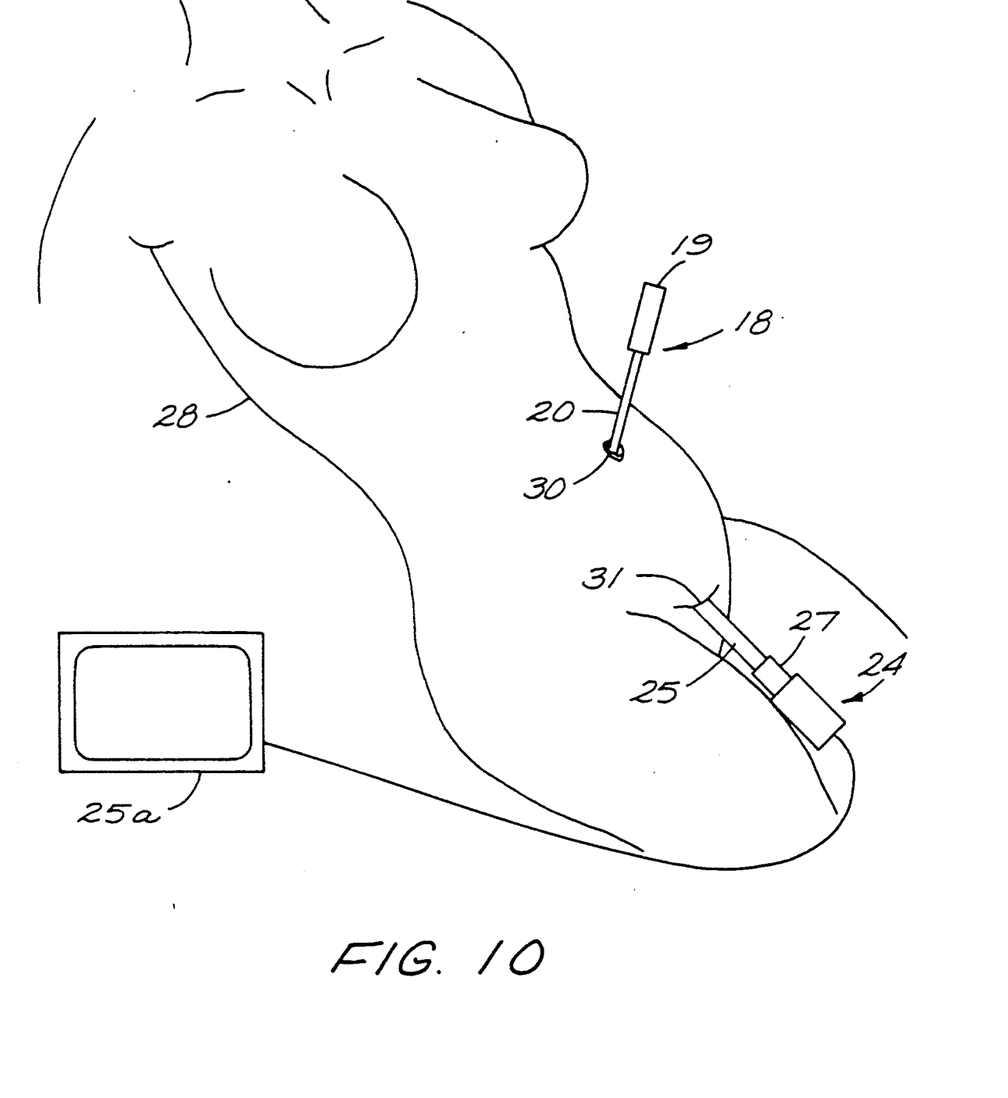
FIG. 10 is a schematic view of a female torso, as in FIG. 9, with the electrosurgical instrument of FIG. 4 inserted through the umbilical incision and the endoscopic tube and viewing instrument inserted through the pubic hair line incision.

The patient 28, after anesthesia, is first given a small (3–4 cm.) vertical incision 30 inside the umbilicus and a short (4 cm.) incision 31 inside the pubic hair line to commence the surgical procedure. Many plastic surgeons have made small or short incisions above the public hair line to take out a small piece of skin and do a limited repair of the muscle and fascia, usually below the umbilicus, and using sutures. There have been no reports of plastic surgeons using endoscopic assistance to accomplish the dissection through such a small incision. Endotube 25 is inserted into incision 31 staying just above the fascia of the interior abdominal wall and below the subcutaneous tissue and fat. The endoscopic tube 27 is introduced to verify position of the surgical instruments and to inspect for bleeding.

Electrosurgical instrument 18 has its cauterizing and cutting tip 20 introduced through umbilical incision 30 and manipulated to undermine the skin for a considerable distance around the incision 30. The cutting and cauterizing by instrument 18 is observed on monitor 25a through endoscopic viewing tube 27. Views of the actual procedure are shown in FIGS. 15–18, below.

Figure 11:
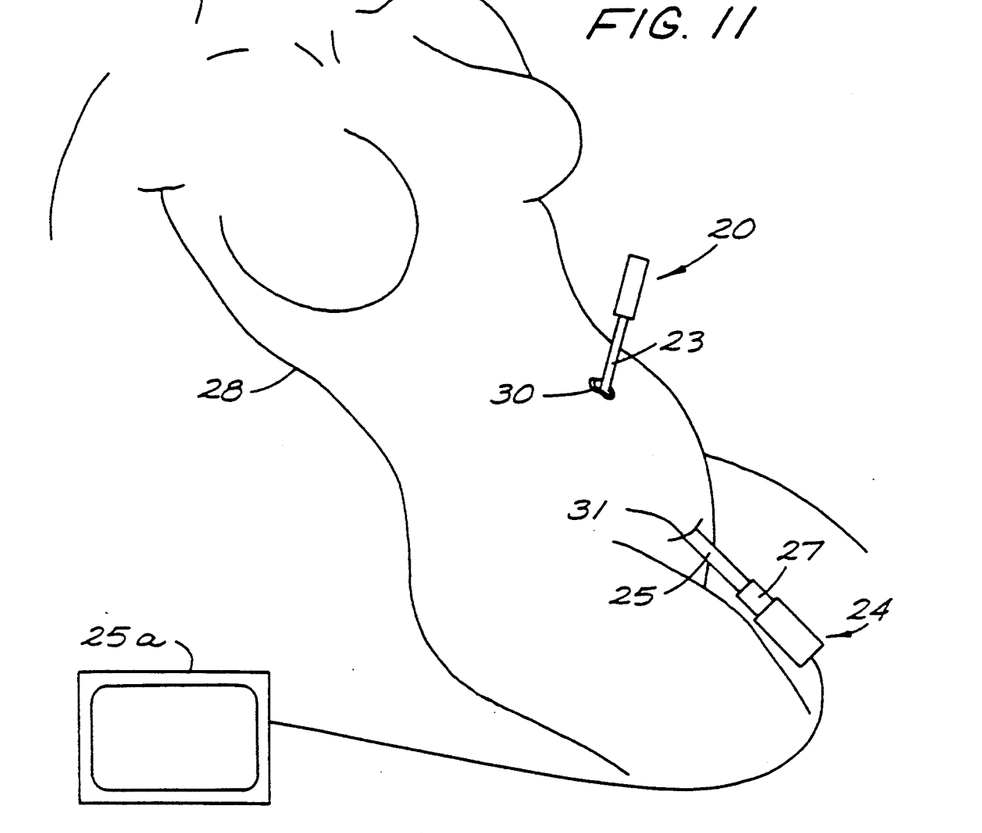
FIG. 11 is a schematic view of a female torso, as in FIG. 10, with the electrosurgical instrument of FIG. 4 removed and the liposuction instrument of FIG. 5 inserted through the umbilical incision and the endoscopic tube and viewing instrument inserted through the pubic hair line incision.
Figure 12:
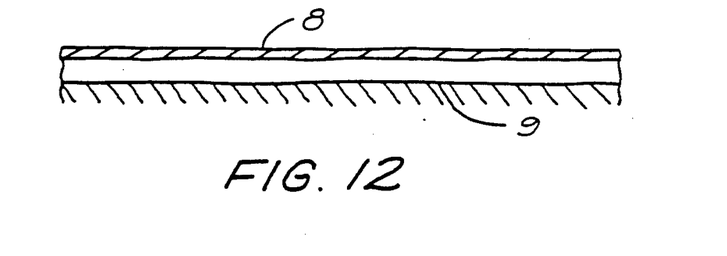
FIG. 12 is a sectional view through the skin, fascia and muscle portion of a body undergoing this surgical procedure and showing the undermining of the skin and separation of the skin layer from the underlying fascia.
Figure 13:
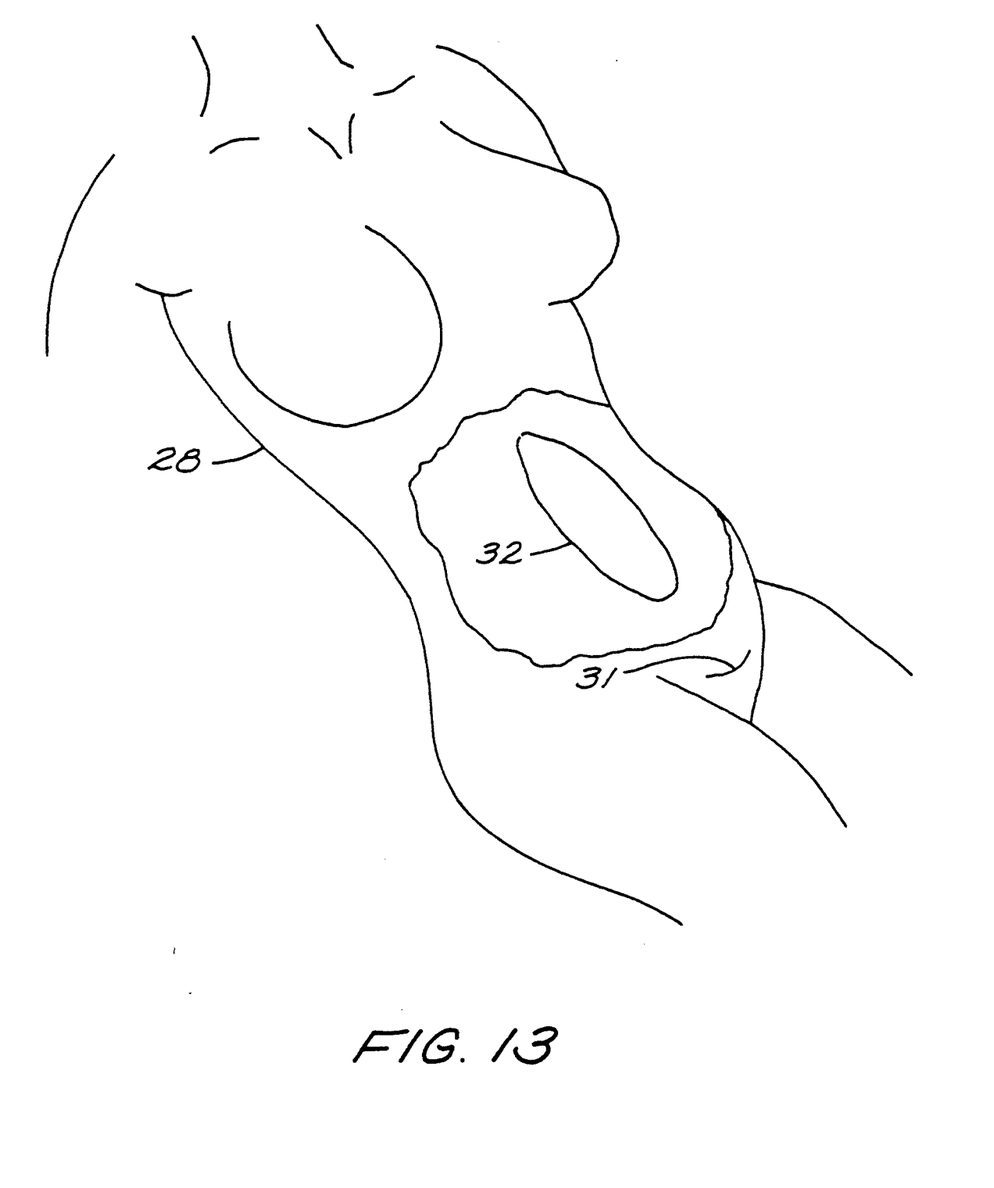
FIG. 13 is a view of a female torso, broken away in front to show the underlying fascia and the marking applied in preparation for plication and stapling.

After completely undermining the area of skin below which the procedure is to be carried out, electrosurgical instrument 18 is withdrawn and liposuction instrument 20 has its tip 23 inserted through umbilical incision 30 and the fat aspirated out through opening 23 by vacuum (not shown). In most cases, liposuction is a necessary step in the procedure since the removal of fat is required for efficient plication of the underlying fascia and muscle. However, if a patient is especially lean and has little or no subcutaneous fat, but requires the abdominoplasty because of muscular separation, the liposuction may be omitted. In traditional abdominoplasties, liposuction is not used because of the bleeding caused by the large incision through the abdomen.

Many plastic surgeons have used liposuction as an adjunct to an abdominoplasty, however in a fully undermined abdominoplasty (as done with this Endoscopic Technique) when done through the standard long incision, full and complete liposuction of the abdomen is usually not done due to the loss of blood supply from arteries and veins severed by the long incision. However with this Endoscopic Technique these arteries and veins are not cut, so there is no problem in doing a complete liposuction of the abdomen.

After completion of the surgical separation of the skin layer 8 from the underlying fascia 9 and muscle (FIG. 10) and liposuction (FIG. 11) of the fat layer, the patient is ready for the plication and repair of the fascia and separated rectus muscle. The liposuction instrument is removed from incision 30 but the endoscopic viewing is kept in place in incision 31 to view and control the procedure of plication and stapling. As an preliminary step, an elliptical marking 32 of methylene blue is inscribed on the fascia below the undermined skin and surrounding the separated rectus muscle area which is to be repaired.

Figure 14:
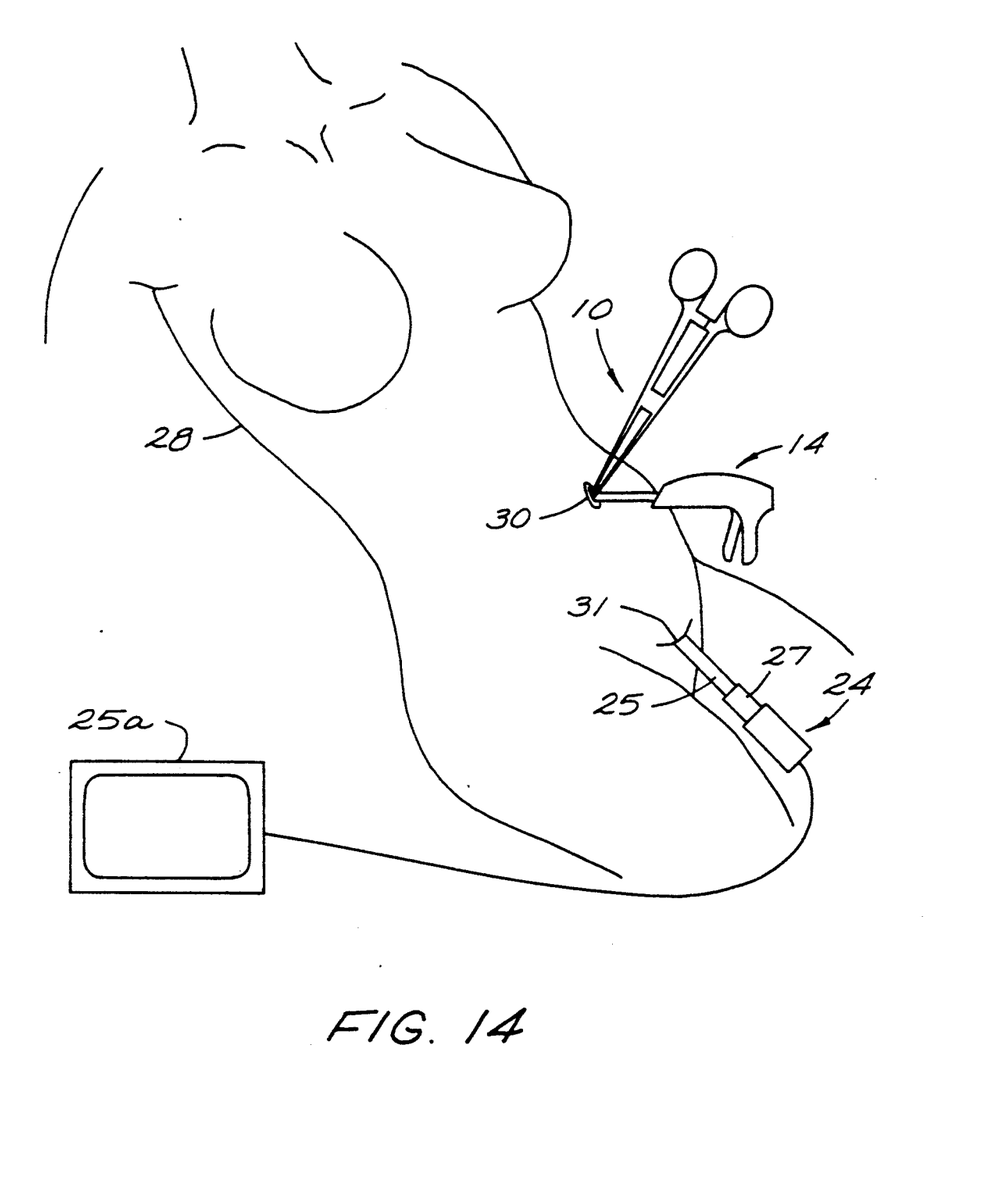
FIG. 14 is a sectional view of a female torso, as in FIG. 8, with the electrosurgical and liposuction instruments removed and the tenaculum of FIG. 2 and the stapling gun of FIG. 3 inserted through the umbilical incision.
Figure 15:
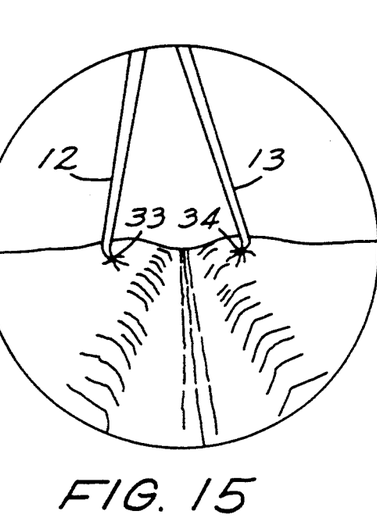
FIG. 15 is a view as seen through the endoscopic viewing instrument of the surgical procedure showing the application of the cervical tenaculum grasping the fascia in preparation for plication and stapling.
Figure 16:
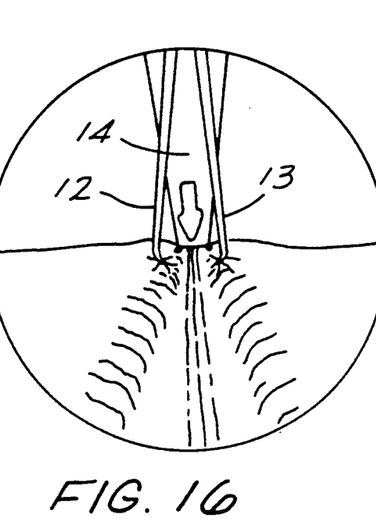
FIG. 16 is a view as seen through the endoscopic viewing instrument of the surgical procedure showing the cervical tenaculum clamping the fascia to plicate it and the stapling gun in place to staple the clamped and plicated portion of the fascia.

The plication and stapling of the fascia and muscle of the abdominal wall is carried out in a sequence of steps shown in FIGS. 14–18. First, as seen in FIG. 14, the cervical tenaculum 10 and tip of the stapling gun 14 are inserted through the umbilical incision 30. The procedure is seen on monitor 25a during all stages. The pointed tips 12 and 13 of tenaculum 10 grip spaced points 33 and 34 (about 12–25 cm. apart) on elliptical mark 32 (FIG. 13) on the abdominal fascia and muscle (FIG. 14).

Then, the tips 12 and 13 are squeezed together (FIG. 16) to begin the plication of the abdominal fascia. The tip of fascial staple gun 14 is pressed against the plicated portion of abdominal fascia adjacent to the squeezed-together tips 12 and 13 of tenaculum 10 and surgical staple 17 inserted into place. The surgical staple 17 penetrates the plicated portion of the fascia and the ends curl into the "B" or "8" configuration shown in FIG. 3. This draws the plicated fascia together and secures it in place. The combiner staple gun/tenaculum mentioned above may also be used in this procedure.

Figure 17:
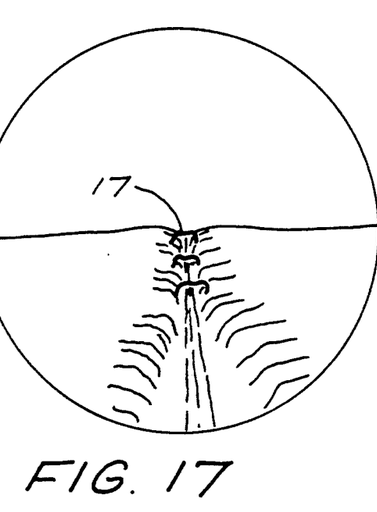
FIG. 17 is a view as seen through the endoscopic viewing instrument of the surgical procedure showing a portion of the clamped and plicated fascia with part of the staples in place.
Figure 18:
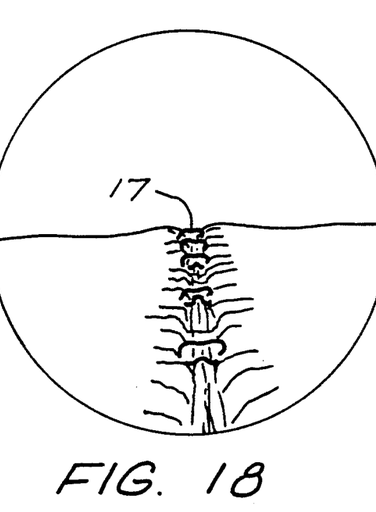
FIG. 18 is a view as seen through the endoscopic viewing instrument of the surgical procedure showing the substantially completed plication and stapling of the fascia in repairing fascial and muscle tissue.
Figure 19:
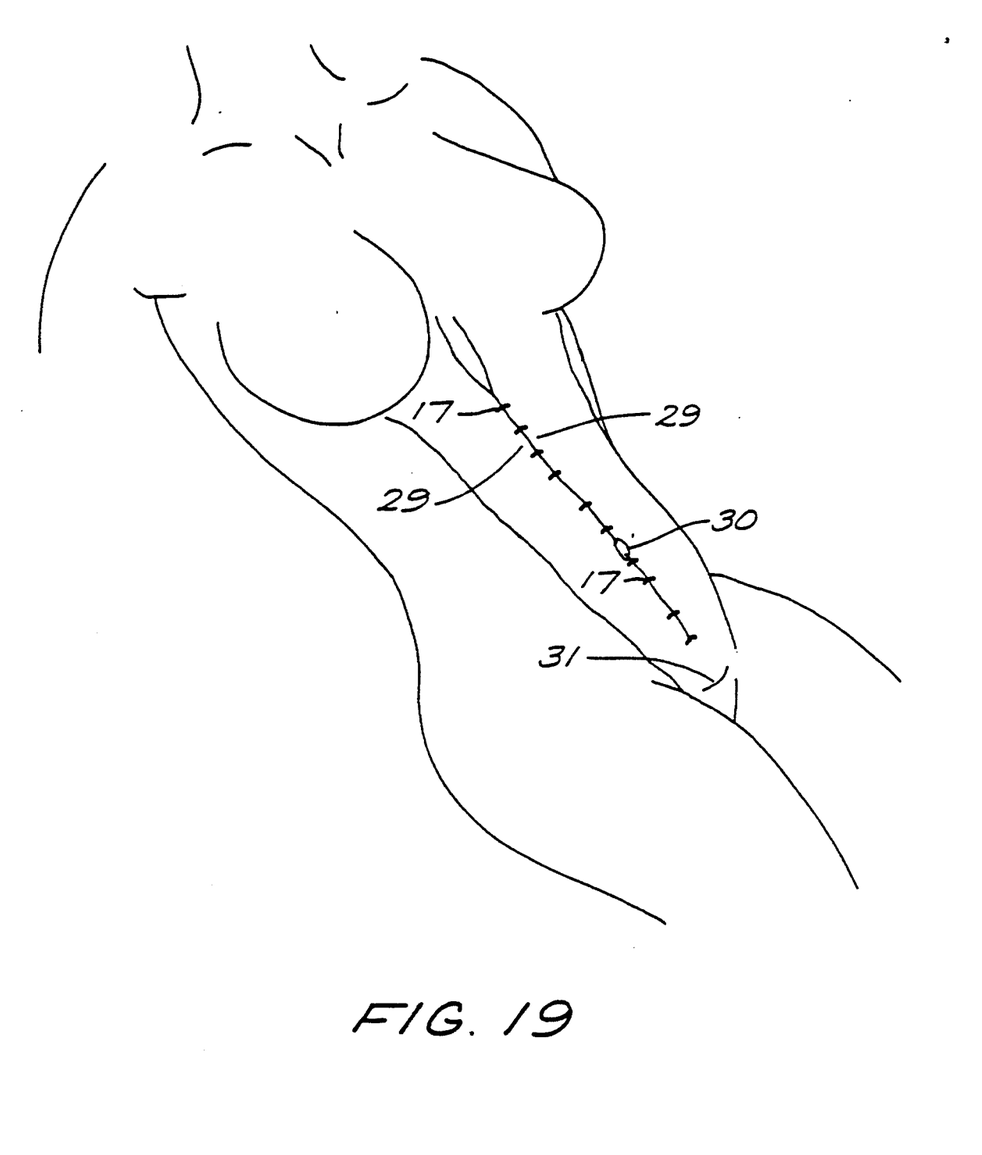
FIG. 19 is a plan view of a patient below the level of the skin showing the completely placated and stapled fascia produced in accordance with FIGS. 15-18.

This procedure is repeated in a series of about plicating and stapling operations at about 4–6 cm. intervals along the placated fascia (FIG. 17). This is followed by plicating and stapling the fascia at points intermediate the 6 cm. spacing to give a closer reinforcing pattern of stapling. Then, the tenaculum 10 is removed and additional staples applied to fill in the spacing of the staples 17 (FIG. 18). In FIG. 19, a view of the fascial and muscular area beneath the skin, similar to FIG. 8, shows the repair of the abdominal rectus muscles 29 by the plication and stapling just described. Typically, forty staples, are applied in making the repair which represents two loads of 20 staples in the stapling gun. In a larger patient, up to 60 staples may be required. If the area of undermining of the skin appears to be insufficient as the conclusion of the plication and stapling procedure, additional undermining may be performed with the cutting and cauterizing instrument 18 as a final procedure.

At the conclusion of the procedure, the umbilical incision 31 and the pubic area incision 30 are then sutured and a cotton ball compress and/or bandage put in place. The patient can go home directly from the recovery room without requiring hospitalization. The natural elasticity of the skin causes the undermined skin to contract or shrink down to the new abdominal wall and adhere to the repaired fascia, thereby not requiring the long incision needed to remove skin and leaving long ugly scars. A six month follow up revealed a full recovery and healing and no loss of the surgical staples.

The results of this new and improved endoscopic assisted abdominoplasty were evaluated on the basis of several procedures performed during May–December 1992.

From the foregoing description, it is seen that, the Endoscopic Assisted Abdominoplasty technique combines several surgical techniques into a completely new procedure to avoid extensive scars on the abdomen:

(1) small incisions hidden in the umbilicus and inside the public hair line.

(2) full and complete undermining of the abdominal skin and fat (as done in the most extensive traditional or standard abdominoplasty) made possible by use of the endoscopic procedure.

(3) complete and effective plication or repair of the muscles and abdominal fascia, from the xyphoid process to the pubis is made possible by use of the endoscope and fascial staples.

(4) does not use sutures to repair the abdominal muscles and fascia as the traditional or standard techniques require.

(5) full and complete liposuction of the abdomen can be done which is contraindicated in the traditional or standard abdominoplasty.

(6) this procedure relies on and allows the natural elasticity of the skin to cause the undermined skin to contract or shrink down to conform to the new abdominal wall, thereby not requiring the long incisions needed to remove skin and leaving long ugly scars.

It should be noted, however, that this Endoscopic Assisted Abdominoplasty is not a procedure for all patients. It is basically for the person (most often women who have had one or more babies) who has weakness in the anterior abdominal muscles (primarily separation of the rectus muscles) and distension of the abdominal fascia. This person may also have additional protrusions of the abdomen due to excessive abdominal fat. However, the person must not have excessive or overhanging abdominal skin where a longer incision is mandatory to remove the excessive skin.

While this invention has been described fully and completely, it should be understood that, within the scope of the appended claims, the invention may be practiced otherwise than as specifically described.

I claim:

1. A surgical abdominoplasty procedure eschewing the use of large abdominal incisions and sutures comprising the steps of
    making a small incision through the umbilicus,
    inserting a surgical cutting and cauterizing instrument through said incision and undermining the skin over a sufficient area of the fascia and muscle to be repaired to permit smooth contraction of the skin over the repaired fascia and muscle,
    inserting a surgical clamping instrument through said incision, underneath the skin and above the fascia, to engage the fascia at predetermined spaced points and operating the clamping instrument to plicate the fascia,
    inserting a fascial stapler through the incision and stapling the plicated fascia with surgical staples,
    repeating the procedure at a predetermined spacing along the fascia being repaired to complete the fascial and muscular repair, and
    suturing or closing the umbilical incision.

2. A surgical abdominoplasty procedure according to claim 1 in which
    the procedure is carried out to effect complete and effective plication and repair of the muscles and abdominal fascia in the region from the xyphoid process to the pubis.

3. A surgical abdominoplasty procedure according to claim 1 in which
    selected portions of the surface of the fascia beneath the undermined skin are marked to define the portions of the fascia to be plicated and stapled in the procedure.

4. A surgical abdominoplasty procedure according to claim 1 in which
    the surface of the fascia beneath the undermined skin is given an elliptical mark to define the portions of the fascia to be plicated and stapled in the procedure, and
    the plication and stapling drawing together and stapling the fascia along said elliptical mark.

5. A surgical abdominoplasty procedure according to claim 1 in which
    a second incision is made within the pubic hair line and an endoscopic tube and endoscopic viewing instrument inserted therein to permit observation of the surgical site during the surgical undermining and plicating and stapling procedures.

6. A surgical abdominoplasty procedure according to claim 1 in which
    fat is removed by liposuction during or after undermining of the skin and prior to plication and stapling.

7. A surgical abdominoplasty procedure according to claim 1 in which
    a further or supplemental undermining of the skin is carried out, as needed, during or after the plication and stapling steps to assure that the skin is undermined a predetermined distance around the fascial and muscular repair and permit subsequent uniform contraction of the skin over the repair.

8. A surgical abdominoplasty procedure according to claim 1 in which
    said surgical cutting and cauterizing instrument is an electrosurgical cutting and cauterizing instrument or a laser instrument operable to be inserted through said incision and undermining the skin over a sufficient area of the fascia and muscle to be repaired to permit smooth contraction of the skin over the repaired fascia and muscle.

9. A surgical abdominoplasty procedure according to claim 1 in which
said surgical clamping instrument is a cervical tenaculum inserted through said incision, underneath the skin and above the fascia, to engage the fascia at predetermined spaced points and operated to plicate the fascia.

10. A surgical abdominoplasty procedure according to claim 1 in which
said fascial stapler is an open end type stapler operable to compressing staples into a closed "B" or "8" shape to secure the plicated fascia.

11. A surgical abdominoplasty procedure according to claim 1 in which
said plication and stapling is done at a spacing of about 4-6 cm. and using about 20-60 staples for the procedure.

12. A surgical abdominoplasty procedure according to claim 1 in which
said surgical clamping instrument is a cervical tenaculum inserted through said incision, underneath the skin and above the fascia, to engage the fascia at distances of about 12-24 cm. and operated to plicate the fascia.

13. A surgical abdominoplasty procedure according to claim 1 in which
said surgical clamping instrument is a cervical tenaculum inserted through said incision, underneath the skin and above the fascia, to engage the fascia at distances of about 12-24 cm. and operated to plicate the fascia,
said fascial stapler is an open end type stapler operable to compressing staples into a closed "B" or "8" shape to secure the plicated fascia, and
said plication and stapling is done at a spacing of about 4-6 cm. and using about 20-60 staples for the procedure.

14. A surgical abdominoplasty procedure according to claim 1 in which
said surgical clamping instrument and said fascial stapler are a single combined instrument for plicating and stapling in sequence.

15. A surgical abdominoplasty procedure according to claim 1 in which
said surgical clamping instrument is a cervical tenaculum and said fascial stapler is an open end type stapler operable to compressing staples into a closed "B" or "8", combined as a single instrument for plicating and stapling in sequence.

16. A surgical abdominoplasty procedure according to claim 1 in which
the procedure is carried out to effect complete and effective plication and repair of the muscles and abdominal fascia in the region from the xyphoid process to the pubis, and
selected portions of the surface of the fascia beneath the undermined skin are marked to define the portions of the fascia to be plicated and stapled in the procedure.

17. A surgical abdominoplasty procedure according to claim 1 in which
the procedure is carried out to effect complete and effective plication and repair of the muscles and abdominal fascia in the region from the xyphoid process to the pubis,
the surface of the fascia beneath the undermined skin is given an elliptical mark to define the portions of the fascia to be plicated and stapled in the procedure, and
the plication and stapling drawing together and stapling the fascia along said elliptical mark.

18. A surgical abdominoplasty procedure according to claim 1 in which
the procedure is carried out to effect complete and effective plication and repair of the muscles and abdominal fascia in the region from the xyphoid process to the pubis,
the surface of the fascia beneath the undermined skin is given an elliptical mark to define the portions of the fascia to be plicated and stapled in the procedure,
the plication and stapling drawing together and stapling the fascia along said elliptical mark, and
a second incision is made within the pubic hair line and an endoscopic tube and endoscopic viewing instrument inserted therein to permit observation of the surgical site during the surgical undermining and plicating and stapling procedures.

19. A surgical abdominoplasty procedure according to claim 1 in which
the procedure is carried out to effect complete and effective plication and repair of the muscles and abdominal fascia in the region from the xyphoid process to the pubis,
the surface of the fascia beneath the undermined skin is given an elliptical mark to define the portions of the fascia to be plicated and stapled in the procedure,
the plication and stapling drawing together and stapling the fascia along said elliptical mark,
a second incision is made within the pubic hair line and an endoscopic tube and endoscopic viewing instrument inserted therein to permit observation of the surgical site during the surgical undermining and plicating and stapling procedures, and
fat is removed by liposuction during or after undermining of the skin and prior to plication and stapling.

20. A surgical abdominoplasty procedure according to claim 1 in which
the procedure is carried out to effect complete and effective plication and repair of the muscles and abdominal fascia in the region from the xyphoid process to the pubis,
the surface of the fascia beneath the undermined skin is given an elliptical mark to define the portions of the fascia to be plicated and stapled in the procedure,
the plication and stapling drawing together and stapling the fascia along said elliptical mark,
a second incision is made within the pubic hair line and an endoscopic tube and endoscopic viewing instrument inserted therein to permit observation of the surgical site during the surgical undermining and plicating and stapling procedures, and
a further or supplemental undermining of the skin is carried out, as needed, during or after the plication and stapling steps to assure that the skin is undermined a predetermined distance around the fascial and muscular repair and permit subsequent uniform contraction of the skin over the repair.

21. A surgical abdominoplasty procedure according to claim 1 in which the procedure is carried out to effect complete and effective plication and repair of the muscles and abdominal fascia in the region from the xyphoid process to the pubis, the surface of the fascia beneath the undermined skin is given an elliptical mark to define the portions of the fascia to be plicated and stapled in the procedure, the plication and stapling drawing together and stapling the fascia along said elliptical mark, a second incision is made within the pubic hair line and an endoscopic tube and endoscopic viewing instrument inserted therein to permit observation of the surgical site during the surgical undermining and plicating and stapling procedures, and a further or supplemental undermining of the skin is carried out, as needed, during or after the plication and stapling steps to assure that the skin is undermined a predetermined distance around the fascial and muscular repair and permit subsequent uniform contraction of the skin over the repair, and fat is removed by liposuction during or after undermining of the skin and prior to plication and stapling.

22. A surgical abdominoplasty procedure according to claim 1 in which the procedure is carried out to effect complete and effective plication and repair of the muscles and abdominal fascia in the region from the xyphoid process to the pubis, the surface of the fascia beneath the undermined skin is given an elliptical mark to define the portions of the fascia to be plicated and stapled in the procedure, the plication and stapling drawing together and stapling the fascia along said elliptical mark, said surgical cutting and cauterizing instrument is an electrosurgical cutting and cauterizing instrument or a laser instrument operable to be inserted through said incision and undermining the skin over a sufficient area of the fascia and muscle to be repaired to permit smooth contraction of the skin over the repaired fascia and muscle, a second incision is made within the pubic hair line and an endoscopic tube and endoscopic viewing instrument inserted therein to permit observation of the surgical site during the surgical undermining and plicating and stapling procedures, and a further or supplemental undermining of the skin is carried out, as needed, during or after the plication and stapling steps to assure that the skin is undermined a predetermined distance around the fascial and muscular repair and permit subsequent uniform contraction of the skin over the repair, and fat is removed by liposuction during or after undermining of the skin and prior to plication and stapling.

23. A surgical abdominoplasty procedure according to claim 1 in which the procedure is carried out to effect complete and effective plication and repair of the muscles and abdominal fascia in the region from the xyphoid process to the pubis, the surface of the fascia beneath the undermined skin is given an elliptical mark to define the portions of the fascia to be plicated and stapled in the procedure, the plication and stapling drawing together and stapling the fascia along said elliptical mark, said surgical cutting and cauterizing instrument is an electrosurgical cutting and cauterizing instrument or a laser instrument operable to be inserted through said incision and undermining the skin over a sufficient area of the fascia and muscle to be repaired to permit smooth contraction of the skin over the repaired fascia and muscle, said surgical clamping instrument is a cervical tenaculum inserted through said incision, underneath the skin and above the fascia, to engage the fascia at predetermined spaced points and operated to plicate the fascia, a second incision is made within the pubic hair line and an endoscopic tube and endoscopic viewing instrument inserted therein to permit observation of the surgical site during the surgical undermining and plicating and stapling procedures, and a further or supplemental undermining of the skin is carried out, as needed, during or after the plication and stapling steps to assure that the skin is undermined a predetermined distance around the fascial and muscular repair and permit subsequent uniform contraction of the skin over the repair, and fat is removed by liposuction during or after undermining of the skin and prior to plication and stapling.

24. A surgical abdominoplasty procedure according to claim 1 in which the procedure is carried out to effect complete and effective plication and repair of the muscles and abdominal fascia in the region from the xyphoid process to the pubis, the surface of the fascia beneath the undermined skin is given an elliptical mark to define the portions of the fascia to be plicated and stapled in the procedure, the plication and stapling drawing together and stapling the fascia along said elliptical mark, said surgical cutting and cauterizing instrument is an electrosurgical cutting and cauterizing instrument or a laser instrument operable to be inserted through said incision and undermining the skin over a sufficient area of the fascia and muscle to be repaired to permit smooth contraction of the skin over the repaired fascia and muscle, said surgical clamping instrument is a cervical tenaculum inserted through said incision, underneath the skin and above the fascia, to engage the fascia at predetermined spaced points and operated to plicate the fascia, said fascial stapler is an open end type stapler operable to compressing staples into a closed "B" or "8" shape to secure the plicated fascia, a second incision is made within the pubic hair line and an endoscopic tube and endoscopic viewing instrument inserted therein to permit observation of the surgical site during the surgical undermining and plicating and stapling procedures, and a further or supplemental undermining of the skin is carried out, as needed, during or after the plication and stapling steps to assure that the skin is undermined a predetermined distance around the fascial and muscular repair and permit subsequent uniform contraction of the skin over the repair, and fat is removed by liposuction during or after undermining of the skin and prior to plication and stapling.

25. A surgical abdominoplasty procedure according to claim 1 in which
    the procedure is carried out to effect complete and effective plication and repair of the muscles and abdominal fascia in the region from the xyphoid process to the pubis,
    the surface of the fascia beneath the undermined skin is given an elliptical mark to define the portions of the fascia to be plicated and stapled in the procedure,
    the plication and stapling drawing together and stapling the fascia along said elliptical mark,
    said surgical cutting and cauterizing instrument is an electrosurgical cutting and cauterizing instrument or a laser instrument operable to be inserted through said incision and undermining the skin over a sufficient area of the fascia and muscle to be repaired to permit smooth contraction of the skin over the repaired fascia and muscle,
    said surgical clamping instrument is a cervical tenaculum inserted through said incision, underneath the skin and above the fascia, to engage the fascia at predetermined spaced points and operated to plicate the fascia,
    said fascial stapler is an open end type stapler operable to compressing staples into a closed "B" or "8" shape to secure the plicated fascia,
    said plication and stapling is done at a spacing of about 4–6 cm. and using about 20–60 staples for the procedure,
    a second incision is made within the pubic hair line and an endoscopic tube and endoscopic viewing instrument inserted therein to permit observation of the surgical site during the surgical undermining and plicating and stapling procedures, and
    a further or supplemental undermining of the skin is carried out, as needed, during or after the plication and stapling steps to assure that the skin is undermined a predetermined distance around the fascial and muscular repair and permit subsequent uniform contraction of the skin over the repair, and
    fat is removed by liposuction during or after undermining of the skin and prior to plication and stapling.

26. A surgical abdominoplasty procedure according to claim 1 in which
    the procedure is carried out to effect complete and effective plication and repair of the muscles and abdominal fascia in the region from the xyphoid process to the pubis,
    the surface of the fascia beneath the undermined skin is given an elliptical mark to define the portions of the fascia to be plicated and stapled in the procedure,
    the plication and stapling drawing together and stapling the fascia along said elliptical mark,
    said surgical cutting and cauterizing instrument is an electrosurgical cutting and cauterizing instrument or a laser instrument operable to be inserted through said incision and undermining the skin over a sufficient area of the fascia and muscle to be repaired to permit smooth contraction of the skin over the repaired fascia and muscle,
    said surgical clamping instrument is a cervical tenaculum inserted through said incision, underneath the skin and above the fascia, to engage the fascia at predetermined spaced points and operated to plicate the fascia,
    said fascial stapler is an open end type stapler operable to compressing staples into a closed "B" or "8" shape to secure the plicated fascia,
    said plication and stapling is done at a spacing of about 4–6 cm. and using about 20–60 staples for the procedure,
    said surgical clamping instrument and said fascial stapler are a single combined instrument for plicating and stapling in sequence,
    a second incision is made within the pubic hair line and an endoscopic tube and endoscopic viewing instrument inserted therein to permit observation of the surgical site during the surgical undermining and plicating and stapling procedures, and
    a further or supplemental undermining of the skin is carried out, as needed, during or after the plication and stapling steps to assure that the skin is undermined a predetermined distance around the fascial and muscular repair and permit subsequent uniform contraction of the skin over the repair, and
    fat is removed by liposuction during or after undermining of the skin and prior to plication and stapling.

27. A surgical abdominoplasty procedure according to claim 1 in which
    the procedure is carried out to effect complete and effective plication and repair of the muscles and abdominal fascia in the region from the xyphoid process to the pubis,
    the surface of the fascia beneath the undermined skin is given an elliptical mark to define the portions of the fascia to be plicated and stapled in the procedure,
    the plication and stapling drawing together and stapling the fascia along said elliptical mark,
    said surgical cutting and cauterizing instrument is an electrosurgical cutting and cauterizing instrument or a laser instrument operable to be inserted through said incision and undermining the skin over a sufficient area of the fascia and muscle to be repaired to permit smooth contraction of the skin over the repaired fascia and muscle,
    said surgical clamping instrument is a cervical tenaculum inserted through said incision, underneath the skin and above the fascia, to engage the fascia at predetermined spaced points and operated to plicate the fascia,
    said fascial stapler is an open end type stapler operable to compressing staples into a closed "B" or "8" shape to secure the plicated fascia,
    said plication and stapling is done at a spacing of about 4–6 cm. and using about 20–60 staples for the procedure,
    said surgical clamping instrument is a cervical tenaculum and said fascial stapler is an open end type stapler operable to compressing staples into a closed "B" or "8", combined as a single instrument for plicating and stapling in sequence,
    a second incision is made within the pubic hair line and an endoscopic tube and endoscopic viewing instrument inserted therein to permit observation of the surgical site during the surgical undermining and plicating and stapling procedures, and
    a further or supplemental undermining of the skin is carried out, as needed, during or after the plication and stapling steps to assure that the skin is undermined a predetermined distance around the fascial and muscular repair and permit subsequent uniform contraction of the skin over the repair, and
fat is removed by liposuction during or after undermining of the skin and prior to plication and stapling.

* * * * *